United States Patent [19]
Håkansson et al.

[11] 4,123,353
[45] Oct. 31, 1978

[54] METHOD AND APPARATUS FOR MEASURING THE CONTENT OF A LOW-MOLECULAR WEIGHT COMPOUND IN A COMPLEX MEDIUM

[75] Inventors: Bo H. Håkansson; Ulf T. G. Nylén; Lars Å. G. Qvarnström, all of Lund, Sweden

[73] Assignee: Gambro AB, Lund, Sweden

[21] Appl. No.: 855,604

[22] Filed: Nov. 29, 1977

[30] Foreign Application Priority Data

Nov. 30, 1976 [SE] Sweden .............................. 76133750

[51] Int. Cl.$^2$ ............................................. D01D 13/00
[52] U.S. Cl. ................................ 210/22 C; 210/96 M; 210/321 A
[58] Field of Search ............... 210/22 C, 96 M, 321 A

[56] References Cited
U.S. PATENT DOCUMENTS

| | | | |
|---|---|---|---|
| 3,441,136 | 4/1969 | Serfass et al. | 210/96 M |
| 3,847,809 | 11/1974 | Kopf | 210/96 M |
| 4,083,777 | 4/1978 | Hutchisson | 210/96 M |

*Primary Examiner*—John Adee
*Attorney, Agent, or Firm*—Lerner, David, Littenberg & Samuel

[57] ABSTRACT

A method and apparatus is provided for measuring the content of a low-molecular weight compound in a complex medium which includes a dialyzer, conduits for conveying the complex medium through the dialyzer and conduits for supplying dialysis fluid to the dialyzer to receive by diffusion a portion of the low-molecular weight compound in the complex medium to produce a dialysate. Apparatus is also provided for conducting the dialysate produced from the dialyzer to a measuring unit, wherein the conducting apparatus includes a main flow line having an enzyme bed and a shunt flow line. A control device is provided for directing the flow of dialysate through the main flow line and the enzyme bed or the shunt flow line, so that the flow of dialysate bypasses the enzyme bed. Apparatus is also provided for comparing the dialysates in the main and shunt flow lines.

10 Claims, 3 Drawing Figures

METHOD AND APPARATUS FOR MEASURING THE CONTENT OF A LOW-MOLECULAR WEIGHT COMPOUND IN A COMPLEX MEDIUM

FIELD OF THE INVENTION

The present invention relates generally to a method and apparatus for measuring the concentration of a low-molecular weight compound in a complex medium, wherein the complex medium is conveyed through a dialyzer, so that a part of the low-molecular weight compound diffuses into the dialysis fluid to produce a dialysate which is conducted to a measuring unit via an enzyme bed.

BACKGROUND OF THE INVENTION

In measuring the concentration of a low-molecular weight compound in a complex medium, such as blood, a dialyzer is employed to produce a dialysate which is then transmitted to an enzyme bed and a measuring unit. However, during such a process, there is a possibility that the measuring unit may be influenced by other factors in the complex medium. For example, if the complex medium is blood and the concentration of low-molecular compound being measured is glucose, there is a possibility that the measuring unit may be influenced by other factors in the blood, other than the glucose, which is broken down by the enzyme bed. Accordingly, it would be advantageous to have the dialysate bypass the enzyme treatment in order that a comparison can be made to determine the zero value.

Accordingly, it is an object of the present invention to provide a method and apparatus for accomplishing the foregoing. Specifically, it is within the contemplation of the present invention to provide a method and apparatus which allows the dialysate to bypass the enzyme treatment at regular intervals so that a comparision can be made and the zero value can be checked.

SUMMARY OF THE INVENTION

Briefly, in accordance with the principles of the present invention, a method and apparatus is provided for measuring the content of a low-molecular weight compound in a complex medium, such as blood. The apparatus includes a dialyzer, conduits for conveying the complex medium through the dialyzer, and conduits for supplying dialysis fluid to the dialyzer to receive by diffusion a portion of the low-molecular weight compound in the complex medium to produce a dialysate. Apparatus is provided for conducting from the dialyzer the dialysate produced to a measuring unit, and such apparatus includes a main flow line having an enzyme bed, and a shunt flow line which bypasses the main flow line and enzyme bed. A control device is provided for directing the flow of dialysate through the main flow line and the enzyme bed, or through the shunt flow line, in order that a comparison of the dialysates may be made.

Advantageously, as a result of the present invention, the flow of dialysate through the enzyme bed can be bypassed at regular intervals in order to check the zero value of the complex medium, such as blood, which may vary, depending on other factors in the blood.

BRIEF DESCRIPTION OF THE DRAWINGS

Further objects, features, and advantages of the present invention will become apparent upon the consideration of the following detailed description of a presently preferred embodiment, when taken in conjunction with the accompanying drawings, wherein.

DETAILED DISCUSSION OF PREFERRED EMBODIMENT OF THE INVENTION

Figure 1:
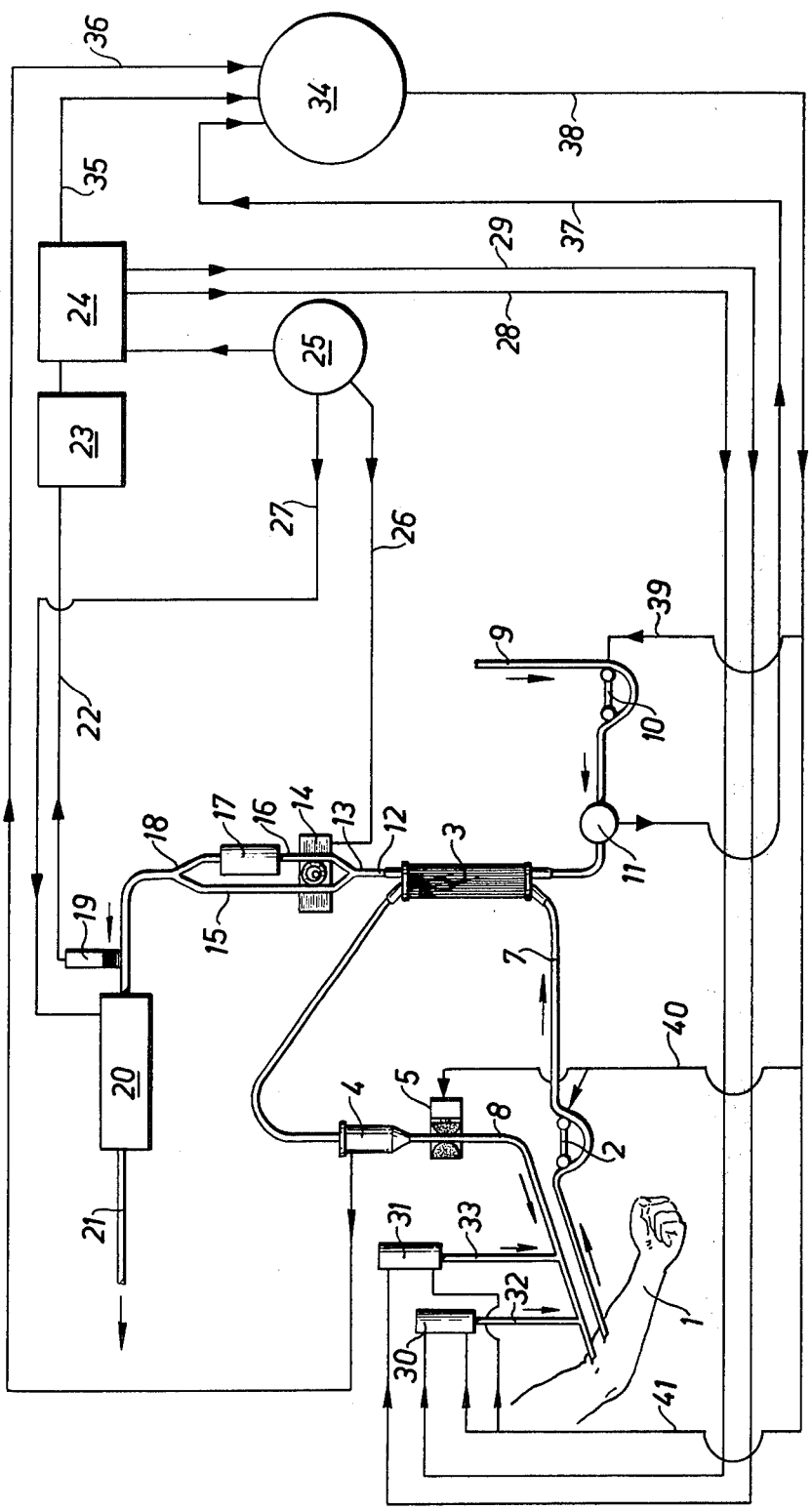
FIG. 1 schematically illustrates a control arrangement incorporating the bypass arrangement of the present invention.

In the embodiment shown, the complex medium is blood which is drawn from a patient 1 and which is pumped by means of a pump 2 through a dialyzer 3 and back to the patient via an air trap 4 and a tube clamp 5. The blood is conducted via an arterial line 7 and a venous line 8.

To those versed in the art, it will be understood that the method and apparatus of the present invention may be employed to examine many other complex media, other than blood. In the following, however, the description is restricted only to blood.

The dialysis fluid is fed to the dialyzer 3 through a line 9 via a pump 10 and a pressure transmitter 11. The dialysis fluid can be conducted through the dialyzer 3 via one, or a small number of fibers, in a manner as described in the above-mentioned patent. The dialysate obtained is then conducted via a line 12 to a branching point 13. From this branching point 13, the dialysate can be conducted with the help of a flow changeover device 14 either through a shunt line 15 or through a main line 16 and an enzyme bed 17 to a merger point 18. The dialysate is then conducted via a measuring unit which, in the example shown, consists of a measuring electrode 19 and a flow meter 20 to a discharge line 21.

Preferably, a dialyzer is chosen which has a substantially smaller volume on the side of the dialysis fluid than on the side of the complex medium to be examined, so that the latter is affected only insignificantly and can be returned to its source. The dialyzer may be constituted, for example, of a fiber dialyzer with only one or a small number of fibers for the conducting of the dialysis fluid, while the medium to be examined is arranged to be conducted outside these fibers. Such a fiber dialyzer is described in detail in U.S. patent application Ser. No. 755,977, filed on Dec. 30, 1976 and is therefore not described in any detail in the present patent application. In said patent application, an analysis procedure is also described which is relevant to the method in accordance with the present invention. With regard to technical details, such as choice of enzyme, dilution, buffers, etc., reference is made to this application and is incorporated herein.

The result obtained in the measuring unit 19 is transmitted via an electric line 22 to an electrometer 23 and further to a computer 24. To this computer 24 are also fed pulses from a clock 25 which also transmits pulses to the flow changeover device 14 and the flow meter 20, respectively. The latter pulses are transmitted via lines 26 and 27, respectively. The computer also controls via lines 28 and 29 the pumping arrangements 30 and 31 which, for example, may supply insulin or glucose via lines 32 or 33, respectively, which open directly into the venous tube 8. Numeral 34 designates an alarm center which may either constitute a separate unit or form part of the computer 24. In the example shown, this alarm unit is designed as a separate unit and therefore receives pulses from the computer 24 via a line 35. It also receives pulses from the air trap 4 via a line 36 and from the pressure transmitter 11 via a line 37. The alarm unit 34 in turn gives off pulses via the line 38 and the branch lines 39, 40, and 41 to the pump 10 for dialysis fluid, the pump 2 and tube clamp 5 for the blood, and the pumps 30 and 31 for insulin and glucose, respectively. In this manner, the whole analytical procedure can be rapidly discontinued if any fault occurs.

In the foregoing, only the most important functions of the arrangement have been described. It will be understood, however, that the system described above may be modified in accordance with whatever is required in the individual case.

Figure 2:
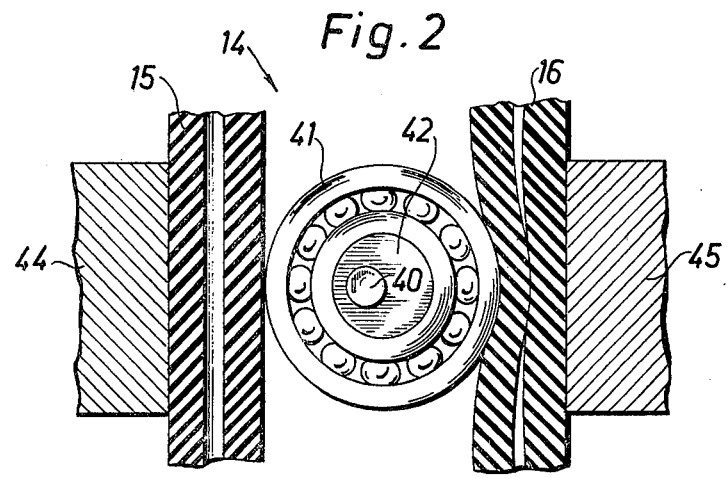
FIG. 2 is a plan view illustrating in detail the device for controlling the flow of dialysate through the main flow line or through the shunt flow line.
Figure 3:
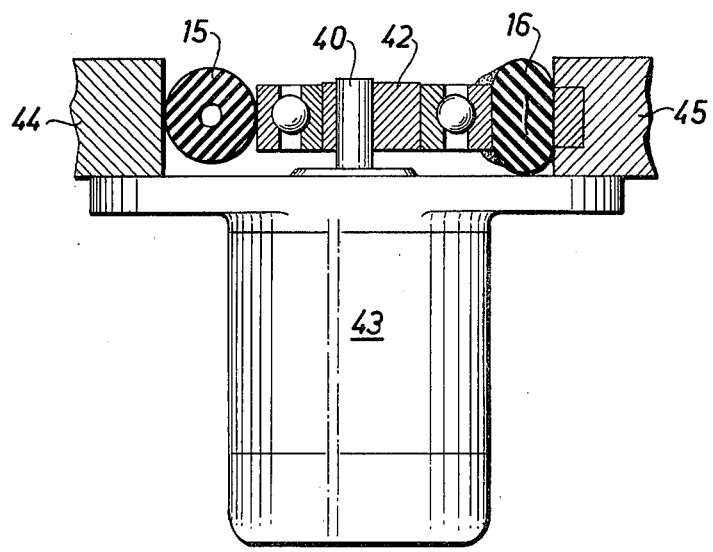
FIG. 3 is an elevational view, in detail, of the apparatus shown in FIG. 2.

There is shown in FIGS. 2 and 3 how the flow changeover device 14 operates in a simple manner by means of a ball bearing 41 supported eccentrically on an axle 40. The support is achieved with the help of an eccentric 42. When the axle 40 is driven by means of the motor 43 shown schematically, either of the tubes 15 or 16 is pressed together. This pressing takes place against supports 44 and 45 which are suitably provided with microswitches (not shown) for the discontinuation of the setting movement or which themselves constitute microswitches for the performance of this function. The motor 43 accordingly receives its pulses from the clock 25 shown in FIG. 1.

If the arrangement in accordance with the invention is used for the measurement of a specific low-molecular weight compound, e.g., glucose in blood, it is possible that the measuring electrode 19 may be influenced by other factors in the blood, other than the glucose broken down by the enzyme bed 17. In accordance with the invention, the enzyme treatment can therefore be discontinued at regular intervals to determine the extent of other elements in the blood. A comparison of the dialysates in the main and shunt flow lines is made. The value obtained from the shunt flow line is then substracted from the value obtained when the glucose is broken down by the enzyme bed in the main flow line to determine the zero value.

Naturally, the invention is not limited solely to the embodiment described above but can be varied within the scope of the following claims. For example, the method and apparatus in accordance with the invention can be supplemented by components of the type described in U.S. patent application Ser. No. 755,977, filed on Dec. 30, 1976.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. Apparatus for measuring the content of a low-molecular weight compound in a complex medium, comprising:
   a dialyzer,
   means of conveying said complex medium through said dialyzer,
   means for supplying dialysis fluid to said dialyzer so that it receives a portion of the low-molecular weight compound by diffusion from said complex medium to produce a dialysate,
   means for conducting the dialysate produced from said dialyzer to a measuring unit,
   said conducting means including a main flow line and a shunt flow line,
   means in at least one of said main and shunt flow lines for effecting said dialysate,
   means for controlling the flow of dialysate through said main flow line and said shunt flow line, and
   means for providing a comparison between the dialysate coming from said main flow line and the dialysate coming from said shunt flow line.

2. Apparatus in accordance with claim 1 wherein said effecting means includes an enzyme bed which is bypassed by a flow of dialysate through said shunt flow line.

3. Apparatus in accordance with claim 1 wherein said controlling means includes means for providing a signal to actuate same.

4. Apparatus in accordance with claim 1 wherein said controlling means includes an eccentrically-mounted element for opening and closing the flow through said main flow line or said shunt flow line.

5. Apparatus in accordance with claim 4 further including means for rotating said eccentrically-mounted element to compress said main flow line or said shunt flow line.

6. Apparatus in accordance with claim 1 wherein said dialyzer includes one or more hollow fibers of a semipermeable membrane material through which said dialysis fluid flows to receive by diffusion said low-molecular weight compound to produce said dialysate.

7. Apparatus in accordance with claim 1 wherein said complex medium is blood and said low-molecular weight compound is glucose.

8. A method for measuring the content of a low-molecular weight compound in a complex medium, comprising the steps of:
   conveying said complex medium through a dialyzer,
   supplying dialysis fluid to said dialyzer so that it receives a portion of the low-molecular weight compound by diffusion from said complex medium to produce a dialysate,
   conducting the dialysate produced from said dialyzer to a measuring unit via a main flow line or a shunt flow line,
   effecting the dialysate in at least one of said main and shunt flow lines, and
   comparing the dialysate coming from said main flow line and the dialysate coming from said shunt flow line.

9. A method in accordance with claim 8 wherein the step of conducting said dialysate through a main flow line includes the step of conducting the dialysate through an enzyme bed located in said main flow line.

10. A method in accordance with claim 7 wherein said complex medium is blood and said low-molecular weight compound is glucose.

* * * * *